(12) United States Patent
Bokade

(10) Patent No.: US 9,988,337 B2
(45) Date of Patent: Jun. 5, 2018

(54) SINGLE STEP PROCESS FOR THE PREPARATION OF BUTYL ACETATE

(71) Applicant: Council of Scientific and Industrial Research, New Delhi (IN)

(72) Inventor: Vijay Vasant Bokade, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days. days.

(21) Appl. No.: 15/510,582

(22) PCT Filed: Sep. 9, 2015

(86) PCT No.: PCT/IN2015/050105
§ 371 (c)(1),
(2) Date: Mar. 10, 2017

(87) PCT Pub. No.: WO2016/038629
PCT Pub. Date: Mar. 17, 2016

(65) Prior Publication Data
US 2017/0283361 A1    Oct. 5, 2017

(30) Foreign Application Priority Data

Sep. 10, 2014 (IN) .......................... 2585/DEL/2014

(51) Int. Cl.
*C07C 67/02* (2006.01)
*C07C 67/03* (2006.01)

(52) U.S. Cl.
CPC .................................. *C07C 67/03* (2013.01)

(58) Field of Classification Search
None
See application file for complete search history.

(56) References Cited

U.S. PATENT DOCUMENTS 1,770,414 A    7/1930    Martin et al.

FOREIGN PATENT DOCUMENTS

| CN | 1583253 | 2/2005 |
| WO | WO-2016038629 | 3/2016 |

OTHER PUBLICATIONS

Ali, Sami H., et al., "Potential biofuel additive from renewable sources—Kinetic study of formation of butyl acetate by heterogeneously catalyzed transesterification of ethyl acetate with butanol", Bioresource Technology, vol. 102, Issue 21, Nov. 2011, pp. 10094-10103, (Nov. 2011), 10094-10103.
Fischer, Emil, et al., "Darstellung der Ester", European Journal of Inorganic Chemistry, 28(3), Oct.-Dec. 1895, 3252-3258 [English translation], (Oct. 1895), 2 pgs.
Ghesti, Grace F., et al., "Biodiesel production via ethylic transesterification with basic zeolites", Quim. Nova., 35(1), 2012, 119-123 [with English translation], (2012), 119-123.
Mat, R., et al., "Catalytic Studies of Boron-HZSM-5 Zeolite for Methane Conversion to Higher Hydrocarbons", Journal of Chemical and Natural Resources Engineering, Special Edition: 146-152, (2008), 146-152.
Namba, S., et al., "Catalytic Application of Hydrophobic Properties of High-Silica Zeolites li. Esterification of Acetic Acid With Butanols", Studies in Surface Science and Catalysis, vol. 20, 1985, pp. 205-211, (Jan. 7, 2009), 205-211.
Ogawa, H., "Transesterification of Esters such as Ethyl Acetate with Alcohols Over Mordenite Type of Zeolite H-Z-HM15", Bulletin of Tokyo Gakugei University Sect. IV, 2004, 56, 53-56, (2004), 53-56.
Wang, Jun, et al., "Preparation and use of heteropolyacid catalyst carried on dealuminized superstable gamma zeolite", English translation of Chinese Publication No. 1583253, published Feb. 23, 2005, (Feb. 23, 2005), 29 pgs.
Zhang, Fumin, et al., "Catalytic performances of heteropoly compounds supported on dealuminated ultra-stable Y zeolite for liquid-phase esterification", China Ser B (2006) 49(2): 140-147, (Apr. 2006), 140-147.
"International Application No. PCT/IN2015/050105, International Search Report and Written Opinion dated Jan. 21, 2016", (Jan. 21, 2016), 9 pgs.
Yufeng, Cong, "An Overview on Synthetic Methods of n-Butyl Acetate", Eur. Chem. Bull, 2012, 1(8), 336-337, (2012), 336-337.

*Primary Examiner* — Clinton A Brooks
*Assistant Examiner* — Ana Z Muresan
(74) *Attorney, Agent, or Firm* — Schwegman Lundberg & Woessner, P.A.

(57) ABSTRACT

The present invention discloses a single step, environmentally and economical viable process for the preparation of butyl acetate from ethyl acetate and n-butanol with high yield using boron loaded zeolite catalyst.

8 Claims, 5 Drawing Sheets

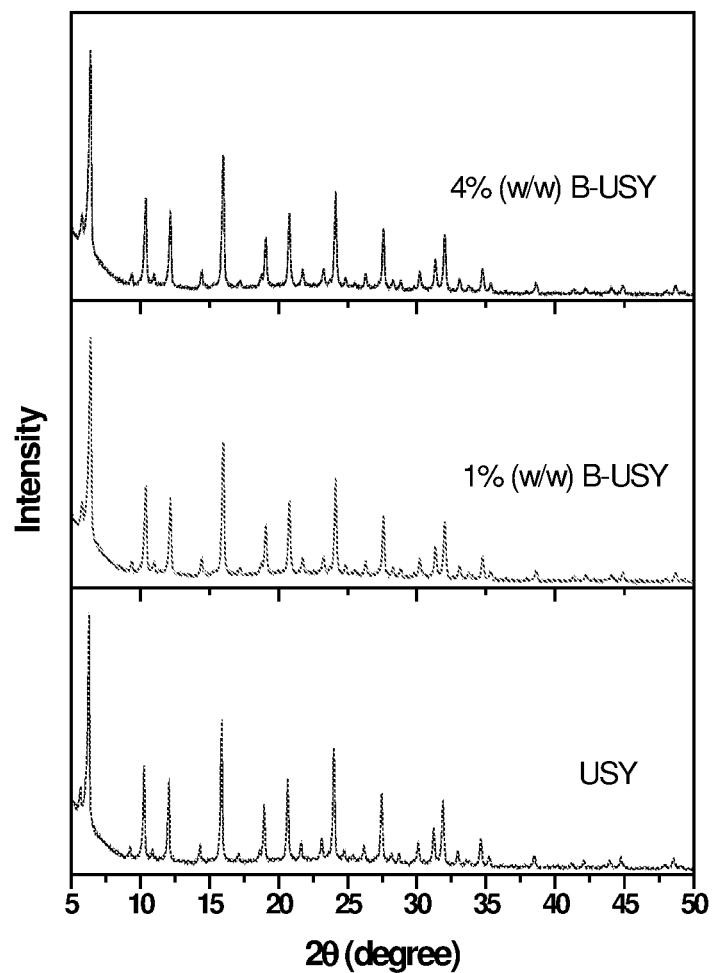
Figure: 1

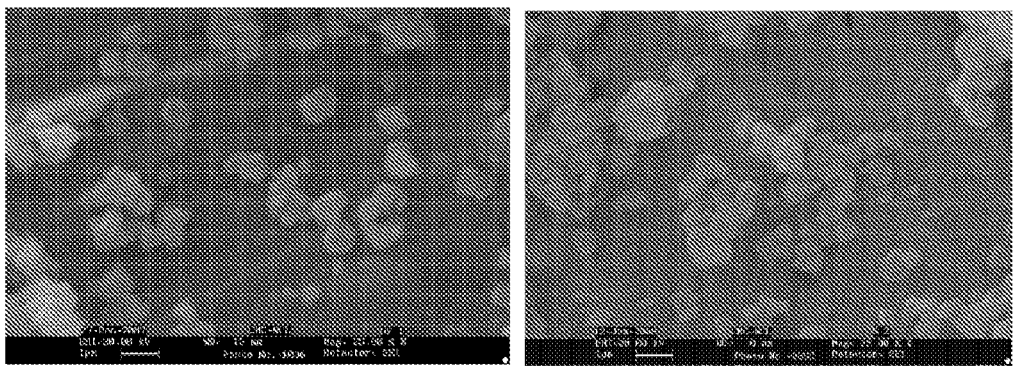
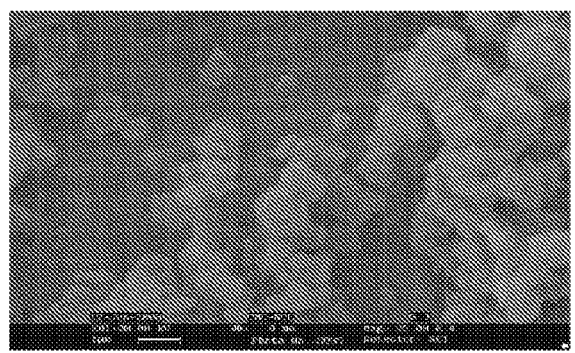
Figure: 2

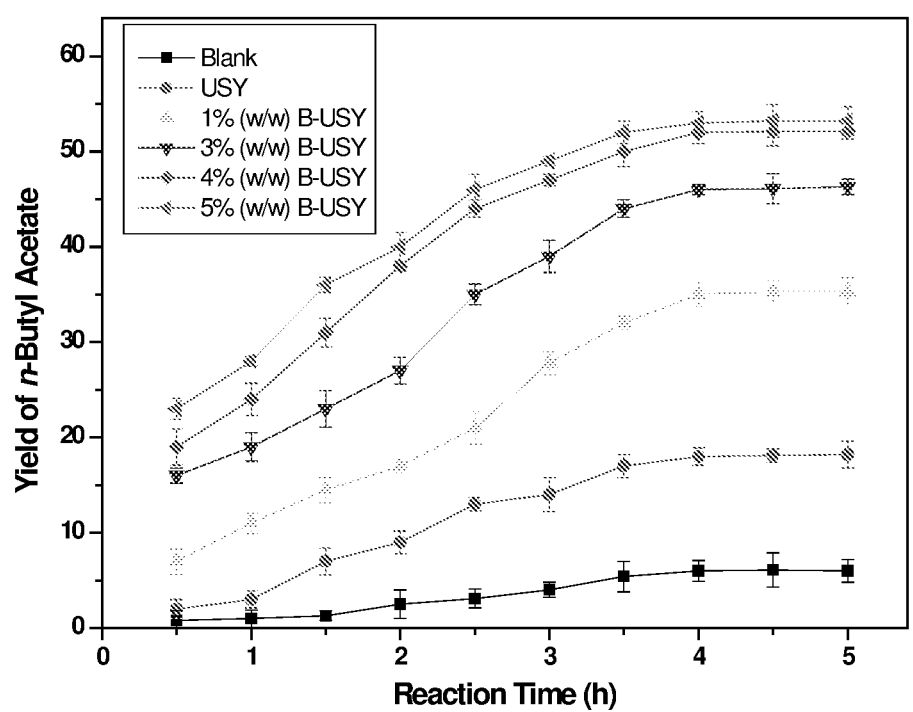
Figure: 3

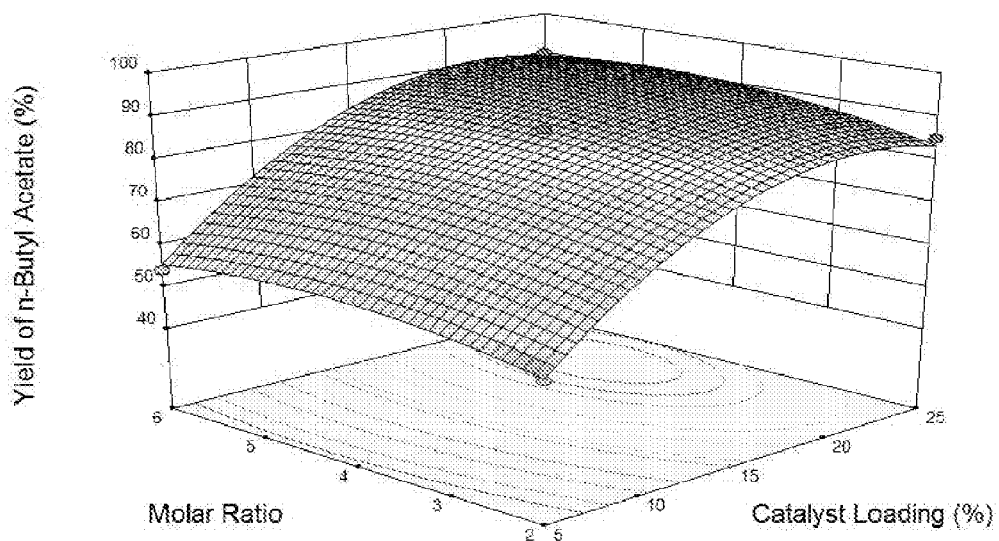
Figure: 4
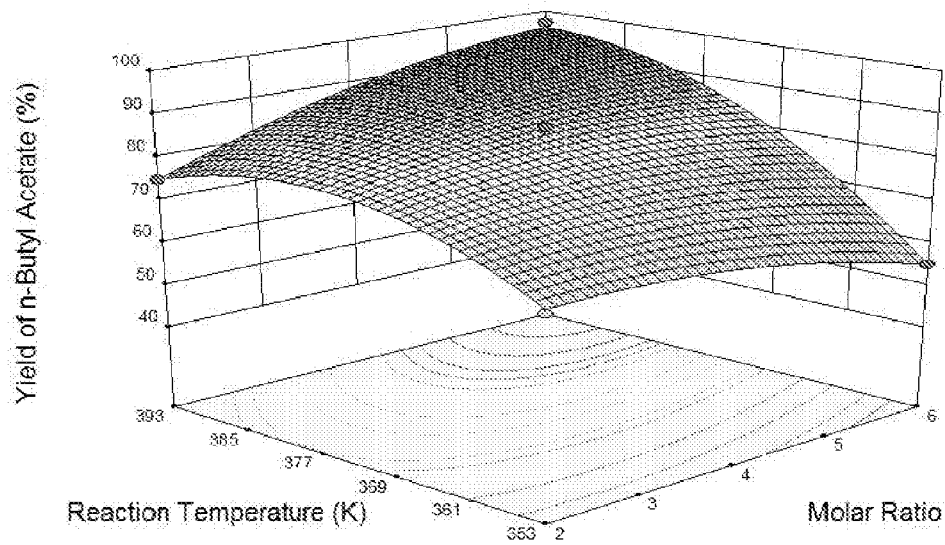
Figure: 5

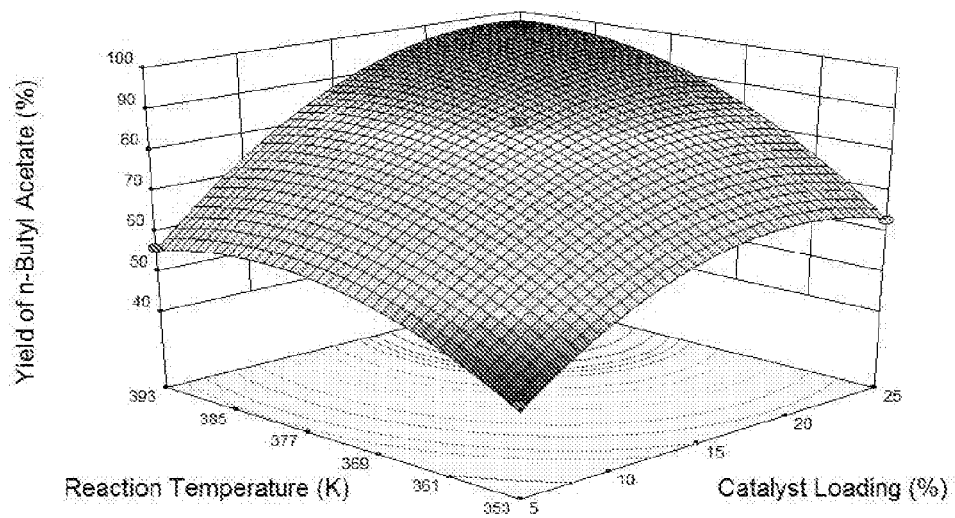
Figure: 6
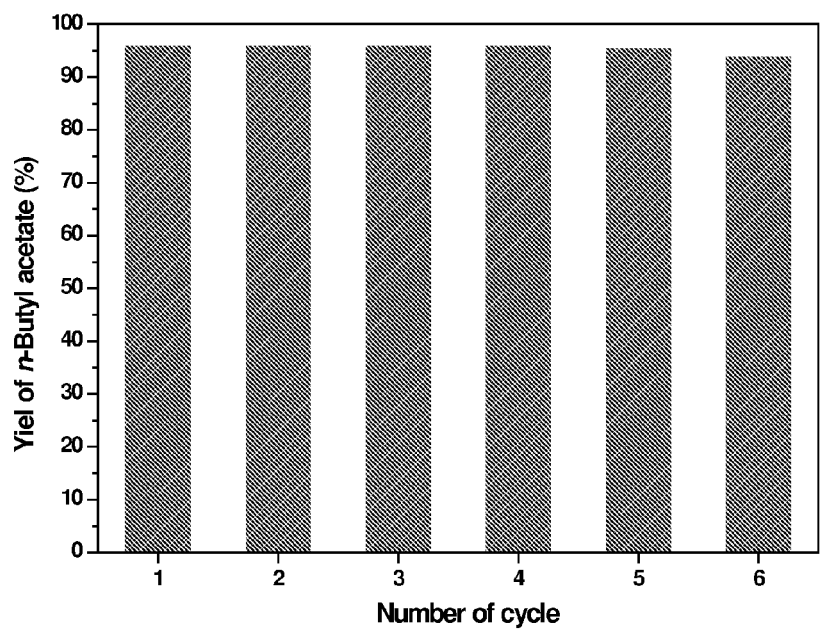
Figure: 7

SINGLE STEP PROCESS FOR THE PREPARATION OF BUTYL ACETATE

PRIORITY CLAIM TO RELATED APPLICATIONS

This application is a U.S. national stage application filed under 35 U.S.C. § 371 from International Application Serial No. PCT/IN2015/050105, which was filed 9 Sep. 2015, and published as WO2016/038629 on 17 Mar. 2016, and which claims priority to India Application No. 2585/DEL/2014, filed 10 Sep. 2014, which applications and publication are incorporated by reference as if reproduced herein and made a part hereof in their entirety, and the benefit of priority of each of which is claimed herein.

FIELD OF THE INVENTION

The present invention relates to a single step process for the preparation of butyl acetate by transesterification reaction of ethyl acetate. More particularly, the present invention relates to a single step, environment friendly process for the preparation of butyl acetate from ethyl acetate and n-butanol with high yield using boron loaded zeolite catalyst.

BACKGROUND AND PRIOR ART OF THE INVENTION

The inevitable depletion of fossil fuel reserves and the subsequent hike in fuel price along with the environmental concerns of conventional fuels has drawn much attention of researchers to develop an industrially and environmentally benign process for production of biofuels and biofuel additives from the renewable resources. Recently, butyl acetate bearing high flash point (22 C) and very low freezing point (−73 C) has been recognized as a potential biofuel additive. Low freezing point (−73 C) of butyl acetate improves the cold flow properties of biodiesel without significantly affecting cetane number and the mixture's heat of combustion. Moreover, its high flash point (22 C) makes it safer to use as biodiesel additive and it also makes superior than the ethyl acetate with flash point of −4 C and similar other biodiesel additives.

Butyl acetate is widely used in pharmaceutical, paint, high-grade paints, inks, resins and acetic acid and solvent dehydration, but also can replace MTBE, a gasoline additive, is a remarkably versatile fine chemicals. Also, butyl acetate holds great potential as a sustainable biofuel additive. Butyl acetate is an important solvent for plastics, resins, gums, and coatings. Butyl acetate can also be used as an extracting agent, as an intermediate in organic synthesis, or in the photographic industry. The traditional production of butyl acetate from acetic acid involves use of butanol as raw materials and sulfuric acid as a catalyst esterification. The disadvantage of this process is existence of serious equipment corrosion, environmental pollution, etc.

Heterogeneously catalyzed transesterification of biobutanol and bioethylacetate can produce butyl acetate. This route is economical, eco-friendly and offers several advantages over the commonly used Fischer Esterification, refer Fischer, E., Speier, A., 1895. Darstellung der Ester. Chemische Berichte 28, 3252-3258. Bio butanol can be made from fermentation of lignocellulosic biomass and bio ethyl acetate through economical renewable ways. Thus transesterification or acetylation of bio ethyl acetate with bio butanol is a sustainable option for renewable butyl acetate production. The co product formed is ethanol which undergoes esterification once again to form ethyl acetate and gets recycled for acetylation. Further, this route does not require special grade (acetic acid resistant) stainless steel equipments and is devoid of serious contamination (associated with the use of homogeneous catalysts) and waste water (formed as product) disposal problems. But, generally, acetylation reaction is slow and is catalyzed by heterogeneous ion exchange resins.

Another route of synthesis of butyl acetate that is well established is the esterification of acetic acid with butanol, but this needs special reactors that are resistant to acetic acid and water is produced as by-product which is wasted.

Article titled "Potential biofuel additive from renewable sources—Kinetic study of formation of butyl acetate by heterogeneously catalyzed transesterification of ethyl acetate with butanol" by S H Ali et al. published in Bioresource Technology, 2011, 102 (21), pp 10094-10103 reports heterogeneously catalyzed transesterification of biobutanol and bioethylacetate to produce butyl acetate. The Amberlite IR 120- and Amberlyst 15 catalyzed transesterification was studied in a batch reactor over a range of catalyst loading (6-12 wt. %), alcohol to ester feed ratio (1:3 to 3:1), and temperature (303.15-333.15 K). This article reports the conversion of butanol up to 75%.

Article titled "Transesterification of Esters such as Ethyl Acetate with Alcohols over Mordenite Type of Zeolite H-Z-HM15" by H Ogava published in Bulletin of Tokyo Gakugei University Sect. IV, 2004, 56, pp. 53-56 reports use of Mordenite type of zeolite H-Z-HM15 catalyst for the transesterification of esters such as ethyl acetate with alcohols. The article reports H-Z-HM15 is the effective catalyst for transesterification of aliphatic acetate such as ethyl acetate and alcohols such as n-butanol and showed its shape selective property for the reaction.

Article titled "Catalytic performances of heteropoly compounds supported on dealuminated ultra-stable Y zeolite for liquid-phase esterification" by F Zhang et al. published in Science in China Series B, 2006, 49 (2), pp 140-147 reports A series of catalysts of 12-Phosphotungstic acid (PW) and its cesium salts immobilized on dealuminated ultra-stable Y zeolite (DUSY). The catalytic activity was improved remarkably by introducing PW onto dealuminated USY (from 49.5% to 86.4%). The supported cesium salt of PW on DUSY catalyst gave a very high conversion of n-butanol of 94.6% and the 100% selectivity for n-butyl acetate.

Chinese patent application no. 1301152 discloses a dealuminated ultra stable Y zeolite catalyst preparation method, Salts miscellaneous loading and its application in the liquid phase esterification reactions. The catalyst is used in the esterification of acetic acid and n-butanol liquid phase reaction, having a low reaction temperature, high conversion rate.

Article titled "Catalytic application of hydrophobic properties of high-silica zeolites ii. esterification of acetic acid with butanols" by S Namba et al. published in Studies in Surface Science and Catalysis, 1985, Volume 20, Pages 205-211 reports liquid-phase esterification of acetic acid with n-, i- or t-butanol on high-silica zeolites. Although, the non-dealuminated HY zeolite was hardly active for the esterification, the dealuminated HY and HZSM-5 zeolites were active and their activities changed with their Si/Al ratios.

Article titled "Catalytic studies of Boron-HZSM-5 zeolite for methane conversion to higher hydrocarbons" by R Mat et al. published in Journal of Chemical and Natural Resources Engineering, Special edition, 2008, pp 146-152 reports the modification of HZSM-5 catalyst with boron in order to reduce the acidity of the catalyst and thus reduce it oxidation activity. A series of boron was loaded into HZSM-5 zeolite via impregnation. Boron oxide covered the active site of HZSM-5 which were responsible for activation of methane thus resulted in lower methane conversion at higher boron loading.

Article titled "Biodiesel production via ethylic transesterification with basic zeolites" by G Ghesti et al. published in Quim. Nova, 2012, Vol. 35, No. 1, pp 119-123 reports Soybean oil transesterification with ethanol in a batch reactor using USY zeolites modified with barium and strontium (15 wt. %) as catalysts. The Ba/USY provided higher conversions (>97%) than Sr/USY (<75%). The increased in catalytic activity of Ba/USY was attributed to two different effects: a larger number of basic sites; and a lower interaction between barium species and HUSY Bronsted sites.

A review article titled "An overview on synthetic methods of n-butyl acetate" by C Yufeng et al. published in Eur. Chem. Bull., 2012, 1(8), 336-337 reports a review of an a few synthetic methods of n-butyl acetate using different catalysts such as inorganic salt like $(Ce(S_2O_8)_2$, $FeNH_4(SO_4)_2.12H_2O$, $LaSO_4/SiO_2$, $KHSO_4$ and $SnC_{14}/C)$, HZSM-5, oxide $(MoO_3/SiO_2)$, $I_2$, heteropolyacid $(H_2(PW_{12}O_{40}).nH_2O)$, quaternary ammonium salt ionic liquid and nanometer ZnO. The review article discussed the maximum yield of n-butyl acetate was 98.5% using $NH_4Fe(SO_4)_2.12H_2O$ as catalyst.

Transesterification of butanol with ethyl acetate can be carried out over homogeneous catalyst, but due to the well-known disadvantages of homogeneous catalysts are reinforced by environmental policies. But none of the prior art processes overcome of drawbacks such as need for specialized equipment, water wastage, adaptable to batch and continuous modes, catalyst leaching amongst.

Thus, it is technological challenge to develop ecofriendly and highly active heterogeneous catalytic process for butyl acetate synthesis. Very limited literature is available on transesterification of butanol with ethyl acetate over heterogeneous catalysts. Accordingly, the present invention develops a single step, environment friendly process for the preparation of butyl acetate from ethyl acetate using boron loaded zeolite catalyst in high yield.

OBJECT OF THE INVENTION

The main objective of the present invention is to provide a single step, environment friendly process for the preparation of butyl acetate from ethyl acetate and n-butanol with high yield using boron loaded zeolite catalyst.

Another objective of the present invention is to provide a catalyst system that facilitates a single step process for the preparation of butyl acetate with high conversion.

SUMMARY OF THE INVENTION

Accordingly, the present invention provides a single step transesterification process for the preparation butyl acetate comprising of heating a reaction mixture of n-butanol, ethyl acetate and boron loaded zeolite (B-USY) catalyst for the period in the range of 1-10 hr, characterized in that yield of butyl acetate is 50-96%.

In still another embodiment of the present invention, ethyl acetate to butanol molar ratio is 1:1 to 1:6.

In another embodiment of the present invention, the process may be batch or continuous and is carried out at temperature in the range of 80-120° C.

In still another embodiment of the present invention, the boron loading in said catalyst is in the range of 1-7%. Preferably the boron loading in said catalyst is 4%.

In yet another embodiment of the present invention, said process involve catalyst loading is in the range of 5-30%. Preferably said process involve catalyst loading is in the range of 20-30%.

In still another embodiment of the present invention, catalyst loading is in the range of 5-30%.

In still another embodiment of the present invention, catalyst loading is in the range of 20-30%.

In still another embodiment of the present invention, the boron loading in said catalyst is in the range of 1-7%.

In still another embodiment of the present invention, the boron loading in said catalyst is 4%.

BRIEF DESCRIPTION OF THE DRAWINGS

FIG. 1: Powder X-ray diffraction patterns of USY, 1% (w/w) B-USY and 4% (w/w) B-USY catalyst FIG. 2: SEM of the catalyst prepared for the synthesis of butyl acetate.

FIG. 3: Catalytic performance of synthesized catalysts for transesterification of ethyl acetate with butanol at catalyst loading of 5%, molar ratio (butanol to ethyl acetate) of 2:1 and reaction temperature of 100° C.

FIG. 4: Response surface and contour plot for synthesis of butyl acetate as a function of molar ratio and catalyst loading at reaction time of 4 h and reaction temperature of 100° C.

FIG. 5: Response surface and contour plot for synthesis of butyl acetate as a function of molar ratio and reaction temperature at reaction time of 4 h and catalyst loading of 15%.

FIG. 6: Response surface and contour plot for synthesis of butyl acetate as a function of catalyst loading and reaction temperature at reaction time of 4 h and molar ratio (butanol to ethyl acetate) of 4:1.

FIG. 7: Reusability of 4% (w/w) B-USY catalyst for the synthesis of butyl acetate at most favorable process parameters: molar ratio of 4:1, catalyst loading of 20%, reaction time of 4 h and reaction temperature of 110 C.

DETAILED DESCRIPTION OF THE INVENTION

Present invention provides a single step, environment friendly, environmentally and economical viable process for the preparation of butyl acetate, offering additional principles of green chemistry and engineering with prospective welfares regarding high catalytic activity (96%, yield of butyl acetate) at milder operating parameters, high catalyst stability and clean synthetic route and devoid of waste byproducts using boron loaded zeolite catalyst.

The present invention provides a single step process for the conversion of ethyl acetate to butyl acetate catalyzed by boron loaded zeolite catalyst, characterized in that boron loading is in the range of 1-7% and yield of butyl acetate is >50%.

The present invention provide a single step trans esterification process for the preparation of butyl acetate comprises of heating the reaction mixture of n-butanol, ethyl acetate and boron loaded zeolite (B-USY) catalyst for the period of 1-10 hr, characterized in the yield of butyl acetate is 96%.

The ratio of ethyl acetate:butanol is in the range of 1:1 to 1:6.

Boron loading in said catalyst is in the range of 1-7% preferably 4%.

The process may be batch or continuous and is carried out at temperature in the range of 80-120° C.

The catalyst loading for said process is in the range of 5-30% preferably 20-30%.

The present invention provides a new heterogeneous catalyst comprising boric acid ($H_3BO_3$) supported on dealuminated HY (USY) for transesterification of ethyl acetate with n-butanol.

The catalyst is prepared by refluxing zeolite with a solution of boric acid solution in water, evaporating the water to obtain a white powder and calcining the powder in air at 500-600° C. for 1-10 hours.

The powder X-ray diffraction patterns of synthesized catalyst is recorded on X-ray diffractometer (P Analytical PXRD system, Model X-Pert PRO-1712) using CuKα radiation at a scanning rate of 0.0671/s in the 2θ ranging from 5 to 50° (FIG. 1).

The nitrogen isotherms (adsorption and desorption) of synthesized catalysts are obtained at low temperature (77 K) with Beckman Coulter SA 3100 analyzer (CA, USA). The calcined sample is degassed at 573 K for 10 h prior to measurements. The specific surface area is calculated using Brunaer-Emmett-Teller (BET) method (Table 1).

The acidity of catalyst is measured by temperature programmed desorption of ammonia (TPD-$NH_3$) with Micromeritics AutoChem (2910, USA) (Table 1). These experiments are performed in a gas-flow system equipped with thermal conductivity detector (TCD). Prior to the measurements, the freshly calcined catalyst sample is dehydrated at 150° C. in high purity (99.995%) helium flow (50 mL $min^{-1}$) for 1 h. The temperature is then reduced to 70° C. and $NH_3$ is permitted to adsorb by exposing catalyst sample to a gas stream encompassing of 10% $NH_3$ in helium for 1 h. The sample is then flushed with helium for another 1 h. The $NH_3$ desorption is performed in helium flow (50 mL $min^{-1}$) by rising the temperature up to 500° C. at heating rate of 10 K $min^{-1}$.

In order to investigate the individual and interactive effects of process variables on the yield of butyl acetate, three-dimensional response surface plots and two-dimensional contour (interaction) plots are drawn (FIGS. 4-6). The three-dimensional surfaces are the graphical illustration of the regression equation (Eq. 2) and each contour curve (two dimensional) represented the combinations of two test variables with the other one maintained at its level of zero (central value). It is found that, the circular contours denotes the negligible interaction between the corresponding variables. On the contrary, the elliptical contours symbolize the significant interactions amongst the relevant variables. The influence of correlation among catalyst loading and molar ratio (FIG. 4), molar ratio and reaction temperature (FIG. 5) and catalyst loading and reaction temperature (FIG. 6) at constant reaction time of 4 h are indicated by 3D response surface plots and 2D contour plots.

From FIG. 4 it is clear that, with increase in loading of 4% (w/w) B-USY catalyst from 5-25% at constant molar ratio (6:1) and reaction temperature (373 K), the yield of butyl acetate found to be increased from 52 to 85%. This is attributed to the increase in catalyst loading makes avail of more catalytically active acid sites for the transesterification reaction (Table 1). This revels that formation of butyl acetate from ethyl acetate involves a more active acid site demanding step. The butyl acetate yield is also observed to be proportional to catalyst amount used; revealing that the reaction proceeds through a pure heterogeneous mechanism.

With increase in molar ratio (butanol:ethyl acetate) from 2:1 to 6:1 at constant catalyst loading of 25%, reaction time of 4 h and reaction temperature of 100 C, the yield of butyl acetate is observed to be slightly increased from 85 to 90%. More dilution of reactants with increase in the molar ratio at limited catalyst active sites does not increase the product formation markedly. This implied that the molar ratio has low influence (p-value of 0.0018) as compared to catalyst loading (p-value of <0.0001) on yield of butyl acetate, indicating that higher yield of butyl acetate may be obtained with lower molar ratio. Hence, to avoid cost associated with separation of unreacted butanol from final product mixture and to make the process industrially benign, low molar ratio is preferred.

The influence of interaction between molar ratio and reaction temperature at constant catalyst loading of 15% and reaction time of 4 h is shown as FIG. 5. The significant interaction effect of molar ratio and reaction temperature is exhibited by ellipse mound shape of two dimensional contour curves (FIG. 5) and it is also evident from low p-value (0.0002) of $X_1X_3$ interaction term. With elevating temperature the yield of butyl acetate is observed to be linearly increased. This is in agreement with the Arrhenius law, a higher temperature results in a higher rate of transesterification leading to higher yield of butyl acetate. The reaction temperature is found to be highly influencing parameter on the yield of butyl acetate and this is also evident from low p-value (<0.0001).

FIG. 6 represents the influence of catalyst loading and reaction temperature on the yield of butyl acetate in 3D response surface and 2D interaction plot at constant molar ratio (butanol to ethyl acetate) of 4:1 and reaction time of 4 h. It is an obvious from FIG. 6 that, at any designated value of reaction temperature from 80 to 120 C, the yield of butyl acetate increased proportionally with catalyst loading. The influence of individual term and interaction term of reaction temperature and catalyst loading perceived to be highly significant on yield of butyl acetate, which is also supported by low p-value.

From this study, catalyst loading and reaction temperature are found to be most contributing terms while molar ratio is least significant term for the transesterification reaction. However, the interaction between catalyst loading and molar ratio has no influence on the response (Y, yield of butyl acetate). Hence, it is highly crucial to develop most favorable reaction parameters for transesterification of ethyl acetate with butanol over 4% (w/w) B/USY in view to obtain maximum yield of butyl acetate.

The most favorable process variable for transesterification of ethyl acetate with butanol over 4% (w/w) B-USY are achieved with numerical technique (numerical algorithm) built in the Design-Expert® Version 8.0.7.1 software. The numerical method examines the design space by the developed model in the analysis to find factor settings that meet the goal of maximizing the percentage yield of butyl acetate (response). The three independent process parameters (Table 2) are fixed in the range among low (−1) and high (+1) while the response (yield of butyl acetate) is set to maximum value. The most favorable (optimum) parameters including the predicted and experimental yield of butyl acetate are presented in Table 4.

The experimental value of yield of butyl acetate showed in table is an average of three independent experiments (Table 4). Yield of butyl acetate of 96% is in fine agreement with the predicted value, with a moderately trivial error of 1.6%. Thus the experimental error is fewer than ±5%, hence the projected statistical model is suitable to predict the yield of butyl acetate by transesterification of butanol with ethyl acetate over 4% (w/w) B-USY.

The reusability of 4% (w/w) B-USY catalyst is evaluated for transesterification of butanol with ethyl acetate at the most favorable process parameters obtained by RSM design (Table 4). After each catalytic run, the catalyst from product mixture is separated by centrifugation and used for proceeding cycle without any post-treatment. The 4% (w/w) B-USY catalyst is perceived to be firm for five catalytic cycles (fresh and four reuses) with 96% yield of butyl acetate (FIG. 7). Thereafter, for the sixth cycle marginal decrease in yield of butyl acetate (96-94%) is observed. This implies that the 4% (w/w) B-USY catalyst is highly active, reusable and stable and has a potential of further application.

EXAMPLES

The following examples are given by way of illustration and therefore should not be construed to limit the scope of the invention.

Ultra Stable Y (USY) zeolite having $SiO_2/Al_2O_3$ molar ratio of 30 was procured from Zeolyst, USA. Ethyl acetate (99.8%), butanol (99%) and $H_3BO_4$ were obtained from Sigma-Aldrich (Sigma, St. Louis, USA).

Example 1: Catalyst Synthesis and Characterization

Typically, 60.0 g of USY catalyst was taken into a 1000 ml round bottom flask and then 600 ml of a 0.64% $H_3BO_4$ solution in water was added. The said mixture was refluxed at 90 C for 1 h under magnetic stiffing. Then solvent was evaporated using rotavapor (80 C). The material thus obtained was in white powder form and subjected for the stepwise calcinations in presence of nitrogen at 320 C for 5 h. A calcined material was then obtained with 1% boron content and designated as 1% (w/w) B-USY. Similarly, other borated USY catalysts were prepared with boron content of 3% (w/w) B-USY and 4% (w/w) B-USY and 5% (w/w) B-USY. Powder X-ray diffraction patterns of synthesized catalyst were recorded on X-ray diffractometer (P Analytical PXRD system, Model X-Pert PRO-1712) using CuKα radiation at a scanning rate of 0.067I/s in the 2θ ranging from 5 to 50° (FIG. 1). Nitrogen isotherms (adsorption and desorption) of synthesized catalysts were obtained at low temperature (77 K) with Beckman Coulter SA 3100 analyzer (CA, USA). The calcined sample was degassed at 300 C for 10 h prior to measurements. The specific surface area is calculated using Brunaer-Emmett-Teller (BET) method (Table 1). Acidity of catalyst was measured by temperature programmed desorption of ammonia (TPD-$NH_3$) with Micromeritics AutoChem (2910, USA) (Table 1). These experiments were performed in a gas-flow system equipped with thermal conductivity detector (TCD). Prior to the measurements, the freshly calcined catalyst sample was dehydrated at 150° C. in high purity (99.995%) helium flow (50 mL $min^{-1}$) for 1 h. The temperature was then reduced to 70° C. and $NH_3$ was permitted to adsorb by exposing catalyst sample to a gas stream encompassing of 10% $NH_3$ in helium for 1 h. The sample was then flushed with helium for another 1 h. The $NH_3$ desorption was performed in helium flow (50 mL $min^{-1}$) by rising the temperature up to 600° C. at heating rate of 10 K $min^{-1}$.

TABLE 1

| Physico-chemical properties of catalys | | |
|---|---|---|
| Catalyst | BET Surface Area ($m^2$ $g^{-1}$) | Total Acidity (μmol $g^{-1}$) |
| USY | 839 | 378 |
| 1% (w/w) B-USY | 790 | 511 |
| 3% (w/w) B-USY | 771 | 587 |
| 4% (w/w) B-USY | 765 | 640 |
| 5% (w/w) B-USY | 753 | 662 |

A. Dealuminated HY (USY) catalyst treated with 2.57% $H_3BO_3$ ie (4% B/USY)

60.0 g of dealuminated HY (USY-720) catalyst was taken into a 1000 ml round bottom flask and then 600 ml of a 2.57% $H_3BO_3$ solution in water was added. The said mixture was refluxed at 90° C. for 1 hour under magnetic stirring. Then solvent was evaporated using rota vapour (80° C.). The material thus obtained was in white powder form and then subjected to stepwise calcination in presence of air at 550° C. for 5 h. The calcined material was then obtained with a boron content of 4%.

The same procedure for synthesis was exercised for other boronated USY samples, 2% B/USY and 5% B/USY.

Example 2: Reaction of Transesterification and Analysis

The USY (parent) and different percentage (1-5%) borated USY catalysts were used for transesterification of butanol with ethyl acetate to obtain butyl acetate (renewable biofuel additive). The butanol, ethyl acetate and catalyst were sequentially added into 50 mL two-necked round bottom glass flask fortified with a reflux condenser, a magnetic stirrer and a thermometer. The temperature accuracy of ±0.5 K was maintained with an electric-heated thermostatic oil bath. The reaction is allowed to run for desired time (1-5 h) at the set temperature (80-120° C.) and after completion of reaction the catalyst from liquid product mixture was removed by centrifugation. The obtained liquid product mixture was analyzed with gas chromatography (GC) Chemito GC-1000, capillary column, BP-1 (50 m length and 0.3 mm width) equipped with Flame Ignition Detector (FID) within programmable temperature range of 40° C. to 200° C. by using with Nitrogen as a carrier gas. The GC-MS (Agilent-5977-AMSD) was used to confirm the reaction products.

Example 3 i. Catalyst Characterizations

The synthesized catalysts were characterized by XRD, BET and TPAD. FIG. 1 shows powder X-ray diffraction patterns of USY, 1% (w/w) B-USY and 4% (w/w) B-USY catalysts. The XRD patterns of parent USY and borated USY were found to be fully crystalline without contribution of amorphous phase and also confirmed the phase purity of synthesized catalyst samples. Osiglio and Blanco reported that, boric acid calcined at 320 C presents sharp peaks at 2θ of 14.8° and 27.9°, attributing to boric oxide. These peaks were not found in XRD patterns of borated USY catalysts. This implied that boric oxide was well dispersed on the USY support. The BET surface area of USY was observed to be decreased with boration due to the narrowing of pores by boron species (Table 1). The total acidities of USY and borated USY samples are depicted as Table 1. With increase in percentage boron on USY the acidity was found to be increased. The well dispersed boron species on surface of USY catalyst, as evidenced by XRD, unswervingly participate to the acidity of the catalyst, as the hydration of boron species leads to generation Bronsted acid sites.

ii. Catalytic Performance of Catalysts

The catalytic performance of blank (without catalyst), USY and 1-5% borated USY catalysts at identical set of process parameters: catalyst loading of 5%, molar ratio of butanol to ethyl acetate of 4, reaction temperature of 100° C., reaction time of 0.5-5 h, speed of agitation of 400 rpm and catalysts' average particle size of 82.5 μm are represented as FIG. 2. The blank (thermal) reaction was conducted to see the effect of catalyst. It can be seen from FIG. 2 that, the maximum yield of butyl acetate was obtained at reaction time of 4 h. All the set of experiments were carried out in triplicate and had 2% error as depicted by the error bars in the FIG. 2. The activity trend at reaction time of 4 h follows: 5% (w/w) B-USY (53%)>4% (w/w) B-USY (52%)>3% (w/w) USY (35%)>1% (w/w) B-USY (18%)>USY (6%). All the borated catalysts showed higher activity than the parent USY catalyst; this can be due to higher acidity of borated USY catalysts (Table 1). The 5% (w/w) B-USY catalyst exhibited 1% higher yield of butyl acetate than 4% (w/w) B-USY catalyst. This may attributed to the multilayer formation boron species on USY at higher loading. Hence 4% (w/w) B-USY catalyst exhibiting 52% butyl acetate yield was selected as a potential catalyst. All the experiments were done in kinetically controlled regime excluding internal and external mass transfer resistances, by using average catalyst particle size of 82.5 μm and speed of agitation of 400 rpm. In present study, 4% (w/w) B-USY catalyst was found to be potential catalyst for the synthesis of butyl acetate. Hence, RSM design with BBD is used to investigate influence of various process parameters. The most favorable process parameter in view to maximize the yield of butyl acetate and reusability of 4% (w/w) B-USY catalyst is presented later.

iii. Statistical Analysis of RSM and Influence of Process Parameters a. Development of Regression Model Equation In the present research work, the correlation among response (yield of butyl acetate, Y) and three reaction variables (Table 2) were evaluated by using RSM. All experiments were performed in triplicate at fixed reaction time of 4 h and average value of butyl acetate yield is presented. FIG. 3 implied that there was no noticeable variation among the actual and predicted response values.

TABLE 2

Selected variables and coded levels used in the Box-Behnken design.

| Variables | Symbol | Coded levels | | |
|---|---|---|---|---|
| | | −1 | 0 | +1 |
| Catalyst Loading (wt. % of ethyl acetate) | $X_1$ | 5 | 15 | 25 |
| Molar Ratio (butanol to ethyl acetate) | $X_2$ | 2 | 4 | 6 |
| Reaction Temperature (K) | $X_3$ | 353 | 373 | 393 | b. Analysis of Variance (ANOVA)

Statistical analysis based on the analysis of variance (ANOVA) was employed for fitting second order quadratic model. At confidence level of 95%, the F-value of the model of 323.96 and with very low probability value (p<0.001) implied that the model fitted was highly significant. This also implied that regression model used was the reliable to predict the yield of butyl acetate. The probability values<0.05 (p<0.05) designate significant model terms. In present case $X_1$, $X_2$, $X_3$, $X_1X_2$, $X_2X_3$, $X_1^2$, $X_2^2$ and $X_3^2$ are significant model terms. The statistical significance data corresponding to individual parameter in Table 3 revealed that, linear term of catalyst loading ($X_1$) and reaction temperature ($X_3$) has significant influence on the butyl acetate yield owing to the high F-value and low p-values. The quadratic term of catalyst loading ($X_1$), F-value 407.14 was observed to be more important than the reaction temperature ($X_3$), F-value 239.51 and the molar ratio ($X_2$), F-value 36.88. Moreover, the consequence of interaction between molar ratio and reaction temperature ($X_2X_3$) also influenced the butyl acetate yield expressively (F-value 232.63) as is specified by the p-value (p<0.0001).

TABLE 3

ANOVA for response surface quadratic model.

| Source | Sum of squares | Df | Mean square | F-value | p-value Prob > F |
|---|---|---|---|---|---|
| Model | 4998.24 | 9 | 555.36 | 323.96 | <0.0001 |
| $X_1$ | 2112.5 | 1 | 2112.5 | 1232.29 | <0.0001 |
| $X_2$ | 40.5 | 1 | 40.5 | 23.63 | 0.0018 |
| $X_3$ | 1200.5 | 1 | 1200.5 | 700.29 | <0.0001 |
| $X_1X_2$ | 2.25 | 1 | 2.25 | 1.31 | 0.2896 |
| $X_1X_3$ | 90.25 | 1 | 90.25 | 52.65 | 0.0002 |
| $X_2X_3$ | 272.25 | 1 | 272.25 | 158.81 | <0.0001 |
| $X_1^2$ | 697.96 | 1 | 697.96 | 407.14 | <0.0001 |
| $X_2^2$ | 63.22 | 1 | 63.22 | 36.88 | 0.0005 |
| $X_3^2$ | 410.59 | 1 | 410.59 | 239.51 | <0.0001 |
| Residual | 12.0 | 7 | 1.71 | — | — |
| Lack of Fit | 12.0 | 3 | 4.0 | — | — |
| Pure Error | 0 | 4 | 0 | — | — |
| Cor Total | 5010.24 | 16 | — | — | — |

$R^2$ = 0.9976;
$R^2$-adjusted = 0.9945;
$R^2$-predicted = 0.9617;
CV = 1.76% c. Model Fitting

The regression equation (Eq. (1)) and coefficient of determination ($R^2$) were used to evaluate the suitability/fit of model. A high value of the coefficient of determination ($R^2$=0.9976) indicated an exceptional association among the independent process variables, which also intended that the second order model was precise and at least 99.76% of the variability in the data could be elucidated by the model. The predicted $R^2$ ($R^2$-predicted=0.9617) was in equitable covenant with the adjusted $R^2$ ($R^2$-adjusted=0.9945) and was observed to be very adequate to specify the high implication of the model. Adequate precision (the signal to noise ratio) >4 is suitable. In present investigation, adequate precision ratio of 56.76 an acceptable signal and proved the ability of model to navigate the design space. In addition, a moderately lesser value of the coefficient of variation (CV=1.76%) implied that the model possessed a superior accuracy and the experiments performed were reliable. In present model, a minimum of 3 Lack of Fit degrees of freedom (Df) and 4 Df for 'Pure Error' ensured a validity of 'Lack of Fit' test. These statistical tests along with statistical model fit summary, high determination coefficient, lack of fit tests and with a consecutive model sum of squares indicated that, the nominated model to be reasonable for predicting the response (yield of butyl acetate). This model was further employed to obtain most favorable (optimum) process variables for transesterification reaction aiming to maximize the yield of butyl acetate and to make the process economical and industrially benign.

d. Influence of Process Variables on Yield of Butyl Acetate

In order to investigate the individual and interactive effects of process variables on the yield of butyl acetate, three-dimensional response surface plots and two-dimensional contour (interaction) plots were drawn (FIGS. 4-6). The three-dimensional surfaces are the graphical illustration of the regression equation and each contour curve (two dimensional) represented the combinations of two test variables with the other one maintained at its level of zero (central value). It has been reported that, the circular contours denotes the negligible interaction between the corresponding variables. On the contrary, the elliptical contours symbolize the significant interactions amongst the relevant variables. The influence of correlation among catalyst loading and molar ratio (FIG. 4), molar ratio and reaction temperature (FIG. 5) and catalyst loading and reaction temperature (FIG. 6) at constant reaction time of 4 h are indicated by 3D response surface plots and 2D contour plots.

As can be seen in FIG. 4, with increase in loading of 4% (w/w) B-USY catalyst from 5-25% at constant molar ratio (6:1) and reaction temperature (100 C), the yield of butyl acetate found to be increased from 52 to 85%. This is attributed to the increase in catalyst loading makes avail of more catalytically active acid sites for the transesterification reaction (Table 1). This revels that formation of butyl acetate from ethyl acetate involves a more active acid site demanding step. The butyl acetate yield was also observed to be proportional to catalyst amount used; revealing that the reaction proceeds through a pure heterogeneous mechanism. Also, as specified by low p-value (<0.0001) (Table 4), the catalyst loading is highly significant for transesterification reaction. With increase in molar ratio (butanol:ethyl acetate) from 2:1 to 6:1 at constant catalyst loading of 25%, reaction time of 4 h and reaction temperature of 100 C, the yield of butyl acetate was observed to be slightly increased from 85 to 90%. More dilution of reactants with increase in the molar ratio at limited catalyst active sites would not increase the product formation markedly. This implied that the molar ratio has low influence (p-value of 0.0018) as compared to catalyst loading (p-value of <0.0001) on yield of butyl acetate, indicating that higher yield of butyl acetate could be obtained with lower molar ratio. Hence, to avoid cost associated with separation of unreacted butanol from final product mixture and to make the process industrially benign, low molar ratio should be preferred. However, the interaction effect between molar ratio ($X_2$) and catalyst loading ($X_1$) was found to be insignificant with shape of two dimensional contour curve circular (FIG. 3) and with high p-value (0.2896) of $X_1X_2$ interaction term.

TABLE 4

Most favorable process parameters for trans-esterification of ethyl acetate with butanol over 4% (w/w) B-USY for reaction time 4 h and validation model adequacy

| Process Parameters | Catalyst loading, $X_1$ (wt. %) | Molar ratio butanol to ethyl acetate), $X_2$ | Reaction temperature, $X_3$ (K) | Yield of Butyl acetate, Y (%) |
|---|---|---|---|---|
| Predicted | 19.7 | 4.3 | 383.3 | 97.6 |
| Experimental | 20 | 4 | 383 | 96 |

The influence of interaction between molar ratio and reaction temperature at constant catalyst loading of 15% and reaction time of 4 h is shown as FIG. 5. The significant interaction effect of molar ratio and reaction temperature was exhibited by ellipse mound shape of two dimensional contour curves (FIG. 5) and as was also evident from low p-value (0.0002) of $X_1X_3$ interaction term. With elevating temperature the yield of butyl acetate was observed to be linearly increased. This was in agreement with the Arrhenius law, a higher temperature results in a higher rate of transesterification leading to higher yield of butyl acetate. The reaction temperature was found to be highly influencing parameter on the yield of butyl acetate and this was also evident from low p-value (<0.0001).

FIG. 6 represents the influence of catalyst loading and reaction temperature on the yield of butyl acetate in 3D response surface and 2D interaction plot at constant molar ratio (butanol to ethyl acetate) of 4:1 and reaction time of 4 h. It is an obvious from FIG. 6 that, at any designated value of reaction temperature from 80-120 C, the yield of butyl acetate increased proportionally with catalyst loading. The influence of individual term and interaction term of reaction temperature and catalyst loading perceived to be highly significant on yield of butyl acetate, which was also supported by low p-value (<0.0001).

From this study, catalyst loading and reaction temperature were found to be most contributing terms while molar ratio was least significant term for the transesterification reaction. However, the interaction between catalyst loading and molar ratio has no influence on the response (Y, yield of butyl acetate). Hence, it is highly crucial to develop most favorable reaction parameters for transesterification of ethyl acetate with butanol over 4% (w/w) B/USY in view to obtain maximum yield of butyl acetate.

e. Obtaining Most Favorable Process Parameters by RSM and Model Validation

The most favorable process variable for transesterification of ethyl acetate with butanol over 4% (w/w) B-USY were achieved with numerical technique (numerical algorithm) built in the Design-Expert® Version 8.0.7.1 software. The numerical method examines the design space by the developed model in the analysis to find factor settings that meet the goal of maximizing the percentage yield of butyl acetate (response). The three independent process parameters (Table 2) were fixed in the range among low (−1) and high (+1) while the response (yield of butyl acetate) was set to maximum value. The most favorable (optimum) parameters including the predicted and experimental yield of butyl acetate are presented in Table 4. The experimental value of yield of butyl acetate showed in table is an average of three independent experiments (Table 4). Yield of butyl acetate of 96% is in fine agreement with the predicted value, with a moderately trivial error of 1.6%. Thus the experimental error is fewer than ±5%, hence the projected statistical model was suitable to predict the yield of butyl acetate by transesterification of butanol with ethyl acetate over 4% (w/w) B-USY.

iv. Reusability of Catalyst

The reusability of 4% (w/w) B-USY catalyst was evaluated for transesterification of butanol with ethyl acetate at the most favorable process parameters obtained by RSM design. After each catalytic run, the catalyst from product mixture was separated by centrifugation and used for proceeding cycle without any post-treatment. The 4% (w/w) B-USY catalyst was perceived to be firm for five catalytic cycles (fresh and four reuses) with 96% yield of butyl acetate (FIG. 7). Thereafter, for the sixth cycle marginal decrease in yield of butyl acetate (96-94%) was observed.

This implies that the 4% (w/w) B-USY catalyst is highly active, reusable and stable and has a potential of further application.

v. Box-Behnken Experimental Design

RSM with Design-Expert® Version 8.0.7.1 (Stat-Ease, Inc., Minneapolis, USA) was used to design the experiments for the reaction parameters used for the transesterification of butanol with an ethyl acetate over 4% (w/w) B-USY catalyst to synthesize butyl acetate biofuel additive. The RSM design with three process variables was performed to gain the optimum process parameters for transesterification reaction. The three independent process variables selected were percentage catalyst loading ($X_1$), butanol to ethyl acetate molar ratio ($X_2$) and reaction temperature ($X_3$). The variables and their coded and uncoded values are presented in Table 2. The percentage yield of butyl acetate (Y) was selected as response/target parameter.

The $3^3$ Box-Behnken experimental design (BBD) involving 17 set of experimental runs consisting of 12 factorial points and 5 center points were performed. These fully randomized experiment formulations consist of all possible combinations of the independent variables at all levels.

The interaction between process variables and maximization of response (Y) was performed by second-order quadratic model.

$$Y = \alpha_0 + \sum_{i=1}^{n} \alpha_i X_i + \sum_{i=1}^{n} \alpha_{ii} X_i^2 + \sum_{i=1}^{n-1} \sum_{j=2}^{n} \alpha_{ij} X_i X_j$$

Where, Y is the percentage yield of butyl acetate (response variable). The parameters $X_i$ and $X_j$ are independent process variables. The terms of $\alpha_o$, $\alpha_i$, $\alpha_{ii}$, $\alpha_{ij}$ are the regression coefficient, the linear term and squared term for the process variable i and the interaction terms among variables i and j, respectively. The n is the total number of variables (in this case, n=3) used to study influence on the yield of butyl acetate. Each process variable was coded into levels −1, 0 and +1 and shown in Table 2.

The polynomial equation was used to correlate the response and experimental levels of each factor. The central composite rotatable design was employed to obtain second-order regression coefficients ($R^2$). Its significance of coefficient of regression was evaluated by the value of F-test. The most favorable process parameters for transesterification were achieved by investigating the three dimensional (3D) response surfaces, two dimensional (2D) contour plots and computing the regression equation.

Example 4

Catalyst Characterization
A. Physico-Chemical Properties of USY Catalyst

| Properties | USY |
| --- | --- |
| Molar ratio $SiO_2/Al_2O_3$ | 32 |
| % Crystallinity | >95% |
| Phase | HY |
| Pore Opening | 6.1 Å |
| Particle Size | 0.6-0.7 μm |
| BET Surface Area | 839 m$^2$/g |
| Appearance | White powder |
| Odor | Odorless |
| Ph | Not Applicable |
| Solubility in Water | Negligible |

Advantages of the Invention

Batch and continuous modes possible
Water is not wasted as by product
Conversion rate is high
Recyclable catalyst

I claim:

1. A single step transesterification process for the preparation of butyl acetate comprising heating a reaction mixture of n-butanol, ethyl acetate and boron loaded zeolite B-USY catalyst for the period in the range of 1 to 10 hr, wherein the yield of butyl acetate is 50-96%.

2. The process as claimed in claim 1, wherein ethyl acetate to butanol molar ratio range is 1:1 to 1:6.

3. The process as claimed in claim 1, wherein catalyst loading is in the range of 5-30%.

4. The process as claimed in claim 1, wherein catalyst loading is in the range of 20-30%.

5. The process as claimed in claim 1, wherein the boron loading in said catalyst is in the range of 1-7%.

6. The process as claimed in claim 1, wherein the boron loading in said catalyst is 4%.

7. The process as claimed in claim 1, wherein said reaction is carried out at temperature in the range of 80-120° C.

8. The process as claimed in claim 1, wherein said process is carried out in batch or continuous mode.

* * * * *